(12) United States Patent
Cunningham et al.

(10) Patent No.: US 7,820,149 B2
(45) Date of Patent: Oct. 26, 2010

(54) MODIFIED SORBITAN SILOXANE COMPOSITIONS AND USE THEREOF

(75) Inventors: Corey Cunningham, Larsen, WI (US); Scott W. Wenzel, Neenah, WI (US); Brian M. Langolf, Fond Du Lac, WI (US); Philip E. Kieffer, Winneconne, WI (US); Christopher V. Decker, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/934,567

(22) Filed: Nov. 2, 2007

(65) Prior Publication Data

US 2009/0117174 A1 May 7, 2009

(51) Int. Cl.
*A61Q 19/10* (2006.01)
*A61K 8/894* (2006.01)

(52) U.S. Cl. .................................... 424/70.12; 510/108

(58) Field of Classification Search ............... 424/70.12
See application file for complete search history.

(56) References Cited

U.S. PATENT DOCUMENTS

| | | | |
|---|---|---|---|
| 4,100,324 A | 7/1978 | Anderson et al. | |
| 4,297,290 A | 10/1981 | Stockburger | |
| 5,284,703 A | 2/1994 | Everhart et al. | |
| 5,296,625 A | 3/1994 | O'Lenick, Jr. et al. | |
| 5,350,624 A | 9/1994 | Georger et al. | |
| 5,446,183 A | 8/1995 | O'Lenick, Jr. | |
| 5,646,321 A | 7/1997 | O'Lenick, Jr. | |
| 6,013,813 A | 1/2000 | O'Lenick, Jr. | |
| 6,162,888 A | 12/2000 | Lee et al. | |
| 6,190,678 B1 | 2/2001 | Hasenoehrl et al. | |
| 6,239,290 B1 * | 5/2001 | Buffa et al. ................. | 549/214 |
| 6,338,855 B1 * | 1/2002 | Albacarys et al. ........... | 424/409 |
| 6,388,042 B1 * | 5/2002 | O'Lenick, Jr. ................ | 528/26 |
| 6,946,413 B2 | 9/2005 | Lange et al. | |
| 2003/0129420 A1 | 7/2003 | Schultz et al. | |
| 2004/0063888 A1 | 4/2004 | Bunyard et al. | |
| 2004/0131660 A1 * | 7/2004 | Lange et al. ................. | 424/443 |
| 2006/0008621 A1 | 1/2006 | Gusky et al. | |
| 2006/0276356 A1 | 12/2006 | Panandiker et al. | |

FOREIGN PATENT DOCUMENTS

| | | |
|---|---|---|
| EP | 1618925 A1 | 1/2006 |
| JP | 57209295 A | 12/1982 |
| WO | 0143717 A1 | 6/2001 |
| WO | 02092050 A2 | 11/2002 |
| WO | 03101417 A1 | 12/2003 |
| WO | 2005004834 A1 | 1/2005 |
| WO | 2006096677 A2 | 9/2006 |

OTHER PUBLICATIONS

Giacometti, J., Milin, C., Wolf, N., Giacometti, F. "Process for Preparing Nonionic Surfactant Sorbitan Fatty Acid Esters with and without Previous Sorbitol Cyclization" J. Agric. Food Chem. 1996, 44(12), 3950-3954.*
Simpson et al., J. Am. Chem. Soc., 1698, 90(15), pp. 4093-4095.*
Lochhead, "Wipes: Recently Disclosed Intellectual Property," Cosmetics & Toiletries Magazine, 2007, vol. 122, No. 8, pp. 71-78.
International Search Report and Written Opinion for PCT/IB2008/054451 mailed Oct. 9, 2009.
International Search Report and Written Opinion for PCT/IB2009/054282 mailed May 24, 2010.

* cited by examiner

*Primary Examiner*—Frederick Krass
*Assistant Examiner*—Brian Gulledge
(74) *Attorney, Agent, or Firm*—Armstrong Teasdale LLP

(57) ABSTRACT

The present disclosure generally relates to personal care compositions and wipes. More particularly, the disclosure relates to compositions and wipes for imparting a perceivable aesthetic feel to the skin of a user. To achieve the perceivable aesthetic feel, a modified sorbitan siloxane is incorporated into the compositions and wipes.

25 Claims, No Drawings

MODIFIED SORBITAN SILOXANE COMPOSITIONS AND USE THEREOF

BACKGROUND OF THE DISCLOSURE

The present disclosure generally relates to personal care compositions and wipes. More particularly, the disclosure relates to compositions and wipes for imparting a perceivable aesthetic feel to the skin or hair of a user. To achieve the perceivable aesthetic feel, a modified sorbitan siloxane is incorporated into the compositions and wipes.

Wipes have been used in the personal care industry for numerous years, and generally comprise a low surfactant, high water base for cleaning bodily fluids or wiping up menses. In recent years, however, consumers have begun demanding more out of personal care products, including wipes. For example, various wipes have come into the market containing ingredients for soothing skin or containing actives for disinfecting surfaces.

Another example of a desired wipe property is the delivery of perceivable consumer aesthetics and/or moisturization. However, many skin benefit agents that provide desired aesthetics and/or moisturization properties are hydrophobic. It has thus proven to be difficult, given the generally high amounts of water and small amounts of surfactants present in typical wet wipe solutions, to incorporate such agents into wipes.

Prior attempts to overcome the difficulties involved in incorporating hydrophobic skin benefit agents into aqueous wet wipe solutions include, for example, solubilizing, dispersing, or microemulsifying oils into a wet wipe solution. These techniques have proven very difficult, however, since stability of oil in a water system is extremely difficult to achieve without separation of the oil. Furthermore, oil on a substrate based product can lead to delamination of certain base sheet structures.

The separation issues may be addressed by raising the surfactant concentration in the wet wipe solution, or by incorporating surfactants high in polyethylene glycol (PEG) and/or polypropylene glycol (PPG) to stabilize the oil in the aqueous wet wipe solution over long periods of time. While these approaches may be effective at stabilizing the oil present in the wet wipe solution, there are other drawbacks. In particular, increasing the concentration of surfactant may result in increased irritation to the skin. Additionally, surfactants containing PEG and/or PPG have recently received negative attention from consumer groups.

One alternative approach to the use of oils to achieve good skin feel is to include humectants such as glycerin, in a wipe solution. Although humectants mix easily into water, they generally need to be included in the composition in high levels to achieve the desired benefit, and these high levels can lead to tack or drag, which is not aesthetically pleasing to the consumer.

Another approach for generating the desired wipe aesthetics and/or moisturization is to place an emulsion on the wipe. This approach is typically effective at modifying the feel of both the wipe and the skin. However, the transfer of the emulsion from the wipe to the skin is generally difficult, leading to large amounts of the wipe solution remaining on the wipe and not transferring to the skin. Additionally, the presence of the emulsion may give the composition a greasy feel on the skin, which can be undesirable to consumers. Furthermore, oil present in the emulsion could potentially result in separation issues in an aqueous wipe solution, as discussed above, and could lead to possible delamination of the base sheet over long term storage.

There thus exists a need for an additive that can be incorporated into personal care products and compositions that can easily disperse or dissolve in the composition, while providing good consumer perceptible feel and/or a skin and/or hair health benefit.

SUMMARY OF THE DISCLOSURE

The present disclosure generally relates to personal care compositions and wipes. More particularly, the disclosure relates to compositions and wipes for imparting a perceivable aesthetic feel to the skin or hair of a user. To achieve the perceivable aesthetic feel, a modified sorbitan siloxane is incorporated into the compositions and wipes.

In one aspect, the present disclosure is directed to a wet wipe for imparting a perceivable aesthetic feel to skin. The wipe comprises a wipe substrate; and a liquid composition comprising a modified sorbitan siloxane having the following general Structure 1:

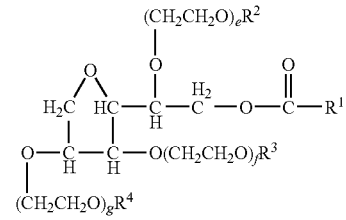

wherein $R^1$ is an alkyl having from 7 to 21 carbon atoms; $R^2$, $R^3$, and $R^4$ are independently selected from the group consisting of H and Structure 2:

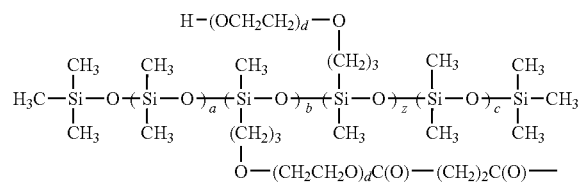

wherein at least one of $R^2$, $R^3$, or $R^4$ is Structure 2; a is an integer ranging from 0 to 200; b is an integer ranging from 1 to 10; z is an integer ranging from 1 to 10; c is an integer ranging from 0 to 10; d is an integer ranging from 5 to 20; n is an integer ranging from 7 to 17; e is an integer ranging from 0 to 30; f is an integer ranging from 0 to 30; g is an integer ranging from 0 to 30, wherein the sum of e, f, and g is an integer ranging from 9 to 50; and wherein the ratio of hydroxyl to carboxyl group ranges from 4:1 to 2:1.

In another aspect, the present disclosure is directed to a composition for imparting a perceivable aesthetic feel to skin or hair, the composition comprising a carrier and a modified sorbitan siloxane having general Structure 1.

In yet another aspect, the present disclosure is directed to a substantially dry wipe for imparting a perceivable aesthetic feel to skin. The substantially dry wipe comprises a wipe substrate; and a composition comprising a modified sorbitan siloxane having general Structure 1.

Other objects and features will be in part apparent and in part pointed out hereinafter.

DETAILED DESCRIPTION OF THE DISCLOSURE

The present disclosure generally relates to personal care compositions and wipes. More particularly, the disclosure relates to compositions and wipes for imparting a perceivable aesthetic feel to the skin or hair of a user. To achieve the perceivable aesthetic feel, a modified sorbitan siloxane is incorporated into the compositions and wipes.

It is often desirable for wipes to deliver good aesthetics to the skin that are perceivable by the consumer. However, prior attempts to improve the aesthetics of wipes, such as wet wipes, have proven difficult. In particular, many skin benefit agents that may act to improve the feel of the wipes are hydrophobic, and thus are difficult to effectively incorporate into wet wipe formulations which typically comprise large amounts of water. Other skin benefit agents, such as humectants, will readily mix with water but need to be incorporated into the wet wipe formulation at high levels in order to be effective, which may result in a tacky or sticky feeling wipe.

In accordance with the present disclosure, it has now been discovered that a perceivable aesthetic feel may be imparted to the skin using a wipe which includes a composition comprising a modified sorbitan siloxane. Advantageously, the modified sorbitan siloxanes used herein are not hydrophobic and thus can readily be incorporated into water-based compositions, such as wet wipe compositions. Furthermore, the presence of the modified sorbitan siloxane in the composition imparts an improved moisturizing, emollient feel, and/or an improved smooth, dry feel to the skin of the user. Unlike other wet wipe compositions which may comprise large amounts of humectant or oil and may feel tacky or greasy on the skin, the compositions of the present disclosure have good tactile properties such as skin glide and a lotion-like feel. Additionally, the modified sorbitan siloxanes enhance the softness perceptions of the wipe, while minimizing the extent of sheet-to-sheet adhesion.

In one aspect, the modified sorbitan siloxanes may be formulated with one or more conventional pharmaceutically-acceptable and compatible carrier materials to form a personal care composition. The composition may take a variety of forms including, without limitation, aqueous solutions, gels, balms, lotions, suspensions, creams, milks, salves, ointments, sprays, foams, solid sticks, aerosols, and the like.

In another aspect, the modified sorbitan siloxanes of the present disclosure may be used in combination with a product, such as a personal care product. More particularly, the modified sorbitan siloxanes may be incorporated into a composition that may be incorporated into or onto a substrate, such as a wipe substrate, an absorbent substrate, a fabric or cloth substrate, or a tissue substrate, among others. For example, the compositions may be incorporated into personal care products, such as wipes, absorbent articles, bath tissues, cloths, and the like. More particularly, the modified sorbitan siloxane-containing composition may be incorporated into wipes such as wet wipes, dry wipes, hand wipes, face wipes, cosmetic wipes, and the like, or absorbent articles, such as diapers, training pants, adult incontinence products, feminine hygiene products, and the like. In one preferred embodiment, the modified sorbitan siloxane-containing composition is a liquid composition that may be used in combination with a wipe substrate to form a wet wipe, or may be a wetting composition for use in combination with a dispersible wet wipe.

Modified Sorbitan Siloxanes

The modified sorbitan siloxanes used herein have the following general Structure 1:

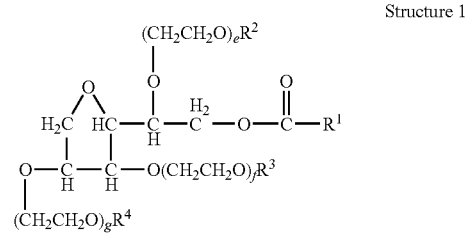

Structure 1 wherein $R^1$ is an alkyl having from 7 to 21 carbon atoms; $R^2$, $R^3$, and $R^4$ are independently selected from the group consisting of H and Structure 2:

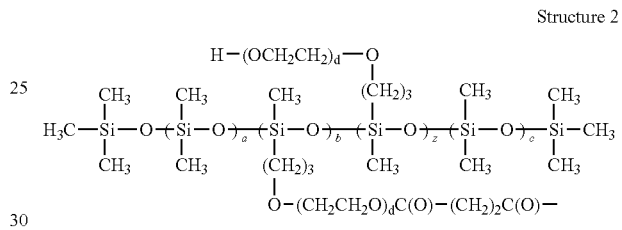

Structure 2 wherein at least one of $R^2$, $R^3$, or $R^4$ is Structure 2; a is an integer ranging from 0 to 200; b is an integer ranging from 1 to 10; z is an integer ranging from 1 to 10; c is an integer ranging from 0 to 10; d is an integer ranging from 5 to 20; n is an integer ranging from 7 to 17; e is an integer ranging from 0 to 30; f is an integer ranging from 0 to 30; g is an integer ranging from 0 to 30, wherein the sum of e, f, and g is an integer ranging from 9 to 50; and wherein the ratio of hydroxyl to carboxyl group ranges from 4:1 to 2:1.

In one aspect, at least two of $R^2$, $R^3$, or $R^4$ is Structure 2. In another aspect, each of $R^2$, $R^3$, and $R^4$ is Structure 2.

In one aspect, the modified sorbitan siloxane has general Structure 1, wherein a is 10, b is 3, z is 1, c is an integer ranging from 0 to 2, d is an integer ranging from 8 to 12, e is an integer ranging from 3 to 17, f is an integer ranging from 3 to 17, and g is an integer ranging from 3 to 17.

In one particular aspect, the modified sorbitan siloxane has general Structure 1 wherein a is 10, b is 3, z is 1, c is 0, d is 8, e is 17, f is 16, g is 17, $R^1$ is 11, and the ratio of hydroxyl to carboxyl group is 3:1.

In another aspect, the modified sorbitan siloxane has general Structure 1 wherein a is 10, b is 3, z is 1, c is 0, d is 8, e is 7, f is 7, g is 7, $R^1$ is 21, and the ratio of hydroxyl to carboxyl group is 4:1.

In another aspect, the modified sorbitan siloxane has general Structure 1 wherein a is 10, b is 3, z is 1, c is 2, d is 12, n is 11, e is 3, f is 3, g is 3, $R^1$ is 11, and the ratio of hydroxyl to carboxyl group is 2:1.

The modified sorbitan siloxanes used herein may be prepared by reacting a dimethicone copolyol with succinic anhydride and polysorbate. More particularly, a two step reaction is performed. A dimethicone copolyol having the following structure:

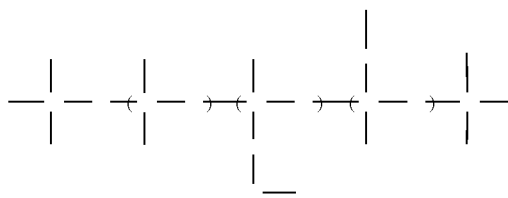

wherein a is an integer ranging from 0 to 200; b is an integer ranging from 2 to 20; and c is an integer ranging from 0 to 10; d is an integer ranging from 5 to 20; and n is an integer ranging from 7 to 17; is first reacted with succinic anhydride having the following structure:

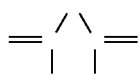

at a temperature of between 50° C. and 100° C., with the mole ratio of the succinic anhydride to hydroxyl group ranging from a value of b/2 to b/5, to produce a carboxyl ester intermediate product having between half and one fifth of the hydroxyl groups esterified. The intermediate product is then reacted with a polysorbate having the following structure:

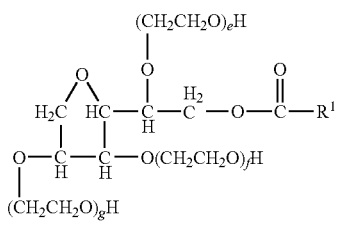

wherein e is an integer ranging from 0 to 30; f is an integer ranging from 0 to 30; g is an integer ranging from 0 to 30; wherein the sum of e, f, and g is an integer ranging from 9 to 50; $R^1$ is alkyl having from 7 to 21 carbon atoms; and wherein the ratio of hydroxyl on the polysorbate to carboxyl groups ranges from 4:1 to 2:1; to produce a modified sorbitan siloxane having general Structure 1.

The resulting compound thus contains a succinate group between the polysorbate and dimethicone copolyol, with the arrangement of polysorbate and dimethicone copolyol units relative to each other being determined by mole ratio of dimethicone copolyol to succinate in step one, and the mole ratio of hydroxyl in the polysorbate to carboxyl in the intermediate product.

Without wishing to be bound to any particular theory, it is believed that the modified sorbitan siloxanes having general Structure 1 and produced as described herein act to improve the aesthetics of personal care compositions and wipes by combining the film forming ability of a dimethicone copolyol with the solubility and skin compatibility of a polysorbate. In particular, the non-hydrophobic nature of the succinate linking the dimethicone copolyol and polysorbate in the modified sorbitan siloxanes of Structure 1 advantageously helps improve the ability of the modified sorbitan siloxanes to mix with aqueous based compositions. Additionally, the presence of an ethoxylated polysorbate, which is less polar than unmodified sorbitan, provides an emollient like-feel to the modified sorbitan siloxane compounds. Furthermore, the modified sorbitan siloxanes comprise a fatty chain, which helps improve skin and/or hair feel, as well as providing a hydrophobic anchor to help deposit the compound onto substrates. Consequently, the modified sorbitan siloxanes of the present disclosure may be readily incorporated into aqueous based compositions, such as wet wipe compositions, while imparting good aesthetics to the composition that are perceivable by the consumer.

Additionally, the modified sorbitan siloxanes may act as emulsifiers to help stabilize the compositions. More particularly, the modified sorbitan siloxanes may assist with solubilizing oil based components or any other hydrophobic skin benefit agents that may be present in the compositions. Furthermore, since the modified sorbitan siloxanes are non-ionic surfactants, the level of additional surfactants typically used in wet wipe compositions may be reduced, thus decreasing the irritation potential of the compositions.

Unlike other solubilizers, such as polysorbate 20, the modified sorbitan siloxanes will also readily transfer to the skin, such as when used in combination with a wipe. As a result, the modified sorbitan siloxane becomes deposited on the skin, where it may act to improve the aesthetic feel of the skin and/or hair. In particular, when the modified sorbitan siloxanes become deposited on the skin and/or hair, they act to improve the softness and feel of the skin and/or hair, and further have a moisturizing effect to soothe rough, dry skin.

Typically, the compositions comprise modified sorbitan siloxanes in an amount of from about 0.05% (by weight of the composition) to about 50.0% (by weight of the composition), more typically from about 0.1% (by weight of the composition) to about 25.0% (by weight of the composition), and more typically from about 0.25% (by weight of the composition) to about 10.0% (by weight of the composition).

As noted above, the modified sorbitan siloxane may be incorporated into personal care compositions and wipes to improve the perceivable aesthetics of these products. In one particular aspect, the present disclosure is directed to wipes. Generally, the wipes of the present disclosure including the modified sorbitan siloxane compounds can be wet wipes or dry wipes. As used herein, the term "wet wipe" means a wipe that includes greater than about 70% (by weight substrate) moisture content. As used herein, the terms "dry wipe" and "substantially dry wipe", used interchangeably herein, mean a wipe that includes less than about 10% (by weight substrate) moisture content. Specifically, suitable wipes for use in the present disclosure can include wet wipes, dry wipes, hand wipes, face wipes, cosmetic wipes, household wipes, industrial wipes, and the like. Particularly preferred wipes are wet wipes, and other wipe-types that include a solution.

Materials suitable for the substrate of the wipes are well know to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter and desirably from about 40 grams per square meter to about 90 grams per square meter.

In one particular embodiment, the wipes of the present disclosure comprise a coform basesheet of polymer fibers and absorbent fibers having a basis weight of from about 45 to about 80 grams per square meter and desirably about 60 grams per square meter. Such coform basesheets are manufactured generally as described in U.S. Pat. Nos. 4,100,324, issued to Anderson, et al. (Jul. 11, 1978); 5,284,703, issued to Everhart, et al. (Feb. 8, 1994); and 5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

The coform basesheet additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

In another embodiment, the wipe substrate may be an airlaid nonwoven fabric. The basis weights for airlaid nonwoven fabrics may range from about 20 to about 200 grams per square meter (gsm) with staple fibers having a denier of about 0.5-10 and a length of about 6-15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference.

In an alternative embodiment, the wipes of the present disclosure can comprise a composite which includes multiple layers of materials. For example, the wipes may include a three layer composite which includes an elastomeric film or meltblown layer between two coform layers as described above. In such a configuration, the coform layers may define a basis weight of from about 15 grams per square meter to about 30 grams per square meter and the elastomeric layer may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

As mentioned above, one type of wipe suitable for use in combination with the modified sorbitan siloxanes is a wet wipe. In addition to the wipe substrate, wet wipes also comprise a liquid composition. The liquid composition can be any liquid, which can be absorbed into the wet wipe basesheet and may include any suitable components, which provide the desired wiping properties. For example, the components may include water, emollients, surfactants, fragrances, preservatives, organic or inorganic acids, chelating agents, pH buffers, or combinations thereof as are well known to those skilled in the art. Further, the liquid may also contain lotions, medicaments, and/or antimicrobials.

The wet wipe composition may desirably be incorporated into the wipe in an add-on amount of from about 10% (by weight of the treated substrate) to about 600% (by weight of the treated substrate), more desirably from about 50% (by weight of the treated substrate) to about 500% (by weight of the treated substrate), even more desirably from about 100% (by weight of the treated substrate) to about 400% (by weight of the treated substrate), and especially more desirably from about 200% (by weight of the treated substrate) to about 300% (by weight of the treated substrate).

The desired liquid composition add-on amounts may vary depending on the composition of the wipe substrate. Typically, however, for coform basesheets, the composition add-on amount will be from about 250% (by weight of the treated substrate) to about 350% (by weight of the treated substrate), and more typically about 330% (by weight of the treated substrate). For air-laid basesheets, the composition add-on amount will typically be from about 200% (by weight of the treated substrate) to about 300% (by weight of the treated substrate), and more typically will be about 235% (by weight of the treated substrate).

These add-on amounts will preferably result in a wet wipe comprising modified sorbitan siloxane in an add-on amount of from about 1.0% (by weight of the treated substrate) to about 5.0% (by weight of the treated substrate), and more preferably from about 1.65% (by weight of the treated substrate) to about 4.95% (by weight of the treated substrate). The add-on amount of modified sorbitan siloxane will depend on the concentration of the modified sorbitan siloxane in the wet wipe composition and the total add-on amount of the composition.

In another embodiment, the wipe is a dry wipe. In this embodiment, the wipe can be wetted with an aqueous solution just prior to, or at the point of, use of the wipe. The aqueous solution can be any aqueous solution known in the art to be suitable for use in wipe products. Generally, the aqueous solution includes mainly water, and can further include additional components, such as cleansers, lotions, preservatives, fragrances, surfactants, emulsifiers, dyes, humectants, emollients, oils, sunscreens, and combinations thereof. The modified sorbitan siloxane may be present in the aqueous solution used to wet the dry wipe prior to use.

Alternately, the dry wipe may be prepared by applying by any suitable means (e.g., by spraying, impregnating, etc.) a composition comprising a modified sorbitan siloxane of the present disclosure onto a wipe substrate. The composition may comprise 100% modified sorbitan siloxane, or alternately, the modified sorbitan siloxane may be present in the composition in combination with a carrier and/or other skin benefit agent, as described herein. In embodiments where the modified sorbitan siloxane-containing composition used to prepare the dry wipe comprises water or moisture, the resulting treated substrate is then dried so that the wipe comprises less than about 10% (by weight substrate) moisture content, and a dry wipe is produced. The treated substrate can be dried by any means known to those skilled in the art including, for example by use of convection ovens, radiant heat sources, microwave ovens, forced air ovens, and heated rollers or cans, or combinations thereof.

The dry wipe may comprise the modified sorbitan siloxane-containing composition in an add-on amount of composition of from about 40% (by weight of the treated substrate) to about 250% (by weight of the treated substrate), more typically from about 75% (by weight of the treated substrate) to about 150% (by weight of the treated substrate) and more typically about 100% (by weight of the treated substrate).

As noted above, the modified sorbitan siloxanes may be incorporated into personal care products such as wipes to improve the perceivable aesthetics of the product. One example of a perceivable aesthetic benefit achieved by incorporating the modified sorbitan siloxanes into a wipe is improved glide of the wipe across the skin as compared to traditional wipe products.

In particular, dynamic coefficient of friction values can be used as an indication of shear forces that occur between the skin and materials that may contact the skin, such as a wipe. Lower dynamic coefficient of friction values indicate lower adhesive forces between the skin and the material, and increased feeling of gentleness of the wipe and improved ability of the wipe to glide across the skin.

Typically, the dynamic coefficient of friction value for a wipe incorporating a modified sorbitan siloxane of the present disclosure will be from about 1.0 to about 3.0, more typically from about 1.2 to about 2.2, and more typically will be about 1.7. Dynamic coefficient of friction may be measured as described in the examples.

In addition to increased gentleness and improved glide of a wipe across the skin, incorporating the modified sorbitan siloxanes into a personal care composition or wipe will also reduce the level of noise that may otherwise occur when the wipe is being used, and will allow the wipe to better drape over the surface of the hand.

In another aspect, inclusion of a modified sorbitan siloxane into a wipe, such as a wet wipe, may desirably lower the sheet-to-sheet adhesion of the wet wipe in the final packaged product, as compared to currently available wipe formulations, by preventing the tendency of two adjacent sheets of wet wipe to adhere to one another. Lower sheet-to-sheet adhesion provides for easier dispensing of the wet wipe. Accordingly, the wet wipes, as disclosed herein, may desirably have a sheet-to-sheet adhesion less than about 7 gf/in. More desirably, the wet wipes may have a sheet-to-sheet adhesion less than about 5 gf/in. Even more desirably, the wet wipes may have a sheet-to-sheet adhesion less than about 3 gf/in.

As noted above, the modified sorbitan siloxanes may also be formulated with one or more conventional pharmaceutically-acceptable and compatible carrier materials to form a personal care composition. The composition may take a variety of forms including, without limitation, aqueous solutions, gels, balms, lotions, suspensions, creams, milks, salves, ointments, sprays, foams, solid sticks, aerosols, and the like. Carrier materials suitable for use in the instant disclosure include those well-known for use in the cosmetic and medical arts as a basis for ointments, lotions, creams, salves, films, aerosols, gels, suspensions, sprays, foams, and the like, and may be used in their art-established levels.

Non-limiting examples of suitable carrier materials include water; glycols such as propylene glycol, butylene glycol, and ethoxydiglycol; lower chain alcohols such as ethanol and isopropanol; glycerin and glycerin derivatives; natural oils such as jojoba oil and sunflower oil; synthetic oils such as mineral oil; silicone derivatives such as cyclomethicone, and other pharmaceutically acceptable carrier materials. As will be recognized by one skilled in the art, the relative amounts of carrier material and other components in the compositions of the disclosure that can be used to formulate the composition will be dictated by the nature of the composition. The levels can be determined by routine experimentation in view of the disclosure provided herein.

In one embodiment, the compositions may comprise water. The compositions can suitably comprise water in an amount of from about 0.1% (by weight of the composition) to about 99% (by weight of the composition), more typically from about 40% (by weight of the composition) to about 99% (by weight of the composition), and more preferably from about 60% (by weight of the composition) to about 99% (by weight of the composition). For instance, where the composition is used in connection with a wet wipe, the composition can suitably comprise water in an amount of from about 75% (by weight of the composition) to about 99% (by weight of the composition).

The compositions may further comprise additional agents that impart a beneficial effect on skin or hair and/or further act to improve the aesthetic feel of the compositions and wipes described herein. Examples of suitable skin benefit agents include emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Thus, in one aspect, the compositions may further optionally include one or more emollient, which typically acts to soften, soothe, and otherwise lubricate and/or moisturize the skin. Suitable emollients that can be incorporated into the compositions include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

Suitable esters could include, but not be limited to, cetyl palmitate, stearyl palmitate, cetyl stearate, isopropyl laurate, isopropyl myristate, isopropyl palmitate, and combinations thereof. The fatty alcohols could include but not be limited to octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

The composition may include one or more emollient in an amount of from about 0.01% (by weight of the composition) to about 70% (by weight of the composition), more desirably from about 0.05% (by weight of the composition) to about 50% (by weight of the composition), and even more desirably from about 0.10% (by weight of the composition) to about 40% (by weight of the composition). In instances wherein the composition is used in combination with a wet wipe, the composition may include an emollient in an amount of from about 0.01% (by weight of the composition) to about 20% (by weight of the composition), more desirably from about 0.05% (by weight of the composition) to about 10% (by weight of the composition), and more typically from about 0.1% (by weight of the composition) to about 5.0% (by weight of the composition).

Sterol and sterol derivatives which are suitable for use in the compositions of the present disclosure include, but are not limited to cholesterol, sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyidecanoate, ergocalciferol, tall oil sterol, soy sterol acetate, lanasterol, soy sterol, avocado sterols, fatty alcohols, and combinations thereof.

The composition of the invention can include sterols, sterol derivatives or mixtures of both sterols and sterol derivatives in an amount of from about 0.01% (by weight of the composition) to about 10% (by weight of the composition), more typically from about 0.05% (by weight of the composition) to about 5% (by weight of the composition), and even more typically from about 0.1% (by weight of the composition) to about 1% (by weight of the composition).

The compositions of the disclosure can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, jojoba oil, maleated soybean oil, meadowfoam oil, palm kernel oil, peanut oil, rapeseed oil, grapeseed oil, safflower oil, sphingolipids, sweet almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof.

The composition of the invention may include fats and oils in an amount of from about 0.01% (by weight of the composition) to about 40% (by weight of the composition), more desirably from about 0.05% (by weight of the composition) to about 25% (by weight of the composition), and even more desirably from about 0.1% (by weight of the composition) to about 10% (by weight of the composition).

Optionally, one or more viscosity enhancers may be added to the composition to increase the viscosity, to help stabilize the composition, such as when the composition is incorporated into a personal care product, thereby reducing migration of the composition and improve transfer to the skin. Suitable viscosity enhancers include polyolefin resins, lipophilic/oil thickeners, ethylene/vinyl acetate copolymers, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, clays, carbomers, acrylic based thickeners, surfactant thickeners, and combinations thereof.

The composition may desirably include one or more viscosity enhancers in an amount of from about 0.01% (by weight of the composition) to about 25% (by weight of the composition), more desirably from about 0.05% (by weight of the composition) to about 10% (by weight of the composition), and even more desirably from about 0.1% (by weight of the composition) to about 5% (by weight of the composition).

The compositions of the disclosure may optionally further comprise rheology modifiers. Rheology modifiers may help increase the melt point viscosity of the composition so that the composition readily remains on the surface of a personal care product and does not substantially migrate into the interior of the product, while substantially not affecting the transfer of the composition to the skin. Additionally, the rheology modifiers help the composition to maintain a high viscosity at elevated temperatures, such as those encountered during storage and transportation.

Suitable rheology modifiers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology modifiers.

The composition of the disclosure can suitably include one or more rheology modifier in an amount of from about 0.1% (by weight of the composition) to about 5% (by weight of the composition).

The compositions of the disclosure may optionally further comprise humectants. Examples of suitable humectants include glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin. The composition of the present disclosure may suitably include one or more humectant in an amount of from about 0.05 (by weight of the composition) to about 25% (by weight of the composition).

The compositions of the disclosure may optionally further comprise moisturizers. Examples of suitable mositurizers include light hydrocarbon oil (e.g., mineral oil, isododecane, petrolatum), vegetable or natural oil (e.g., sunflower oil, olive oil, sweet almond oil, grapeseed oil, corn oil, safflower oil, shea butter, coconut oil, canola oil, castor oil, jojoba oil), hydrogenated vegetable oil (e.g., hydrogenated castor wax, hydrogenated apricot kernel oil, hydrogenated canola oil, hydrogenated jojoba oil, hydrogenated olive oil, hydrogenated sesame seed oil), fatty ester (e.g., octyldodecyl neopentanoate, stearyl stearate, isopropyl myristate, isopropyl palmitate, stearyl behenate, $C_{12}$-$C_{15}$ alkyl benzoate, butyl isostearate, cetyl caprate, cetyl caprylate, ethyl apricot kernelate, ethyl avocadate, ethylhexyl caprate/caprylate, ethylhexyl cocoate, ethylhexyl isopalmitate, isocetyl myristate, isopropyl jojobate, myristyl laurate), fatty acid (e.g. palmitic acid, stearic acid, myristic acid, oleic acid, linoleic acid, behenic acid), fatty alcohol (e.g. lauryl alcohol, cetyl alcohol, stearyl alcohol, behenyl alcohol), or combinations thereof. In one embodiment, the composition may comprise a fatty ester as a carrier. One example of a fatty ester is isopropyl myristate, which is available under the name TEGOSOFT M (Degussa). The composition of the present disclosure may suitably include one or more moisturizer in an amount of from about 0.01% (by weight of the composition) to about 50% (by weight of the composition).

The compositions of the disclosure may optionally further comprise film formers. Examples of suitable film formers include petrolatum, emollient esters, lanolin derivatives (e.g., acetylated lanolins), superfatted oils, cyclomethicone, cyclopentasiloxane, dimethicone, natural and synthetic oils, fatty acids, fatty alcohols, waxes, synthetic and biological polymers, proteins, quaternary ammonium materials, starches, gums, cellulosics, polysaccharides, albumen, acrylates derivatives, IPDI derivatives, and the like. The composition of the present disclosure may suitably include one or more film former in an amount of from about 0.01% (by weight of the composition) to about 20% (by weight of the composition).

The compositions of the disclosure may optionally further comprise slip modifiers. Examples of suitable slip modifiers include bismuth oxychloride, iron oxide, mica, surface treated mica, ZnO, $ZrO_2$, silica, silica silyate, colloidal silica, attapulgite, sepiolite, starches (i.e. corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, bismuth oxychloride, iron oxide, aluminum oxide, silicone resin, barium sulfate, calcium carbonate, cellulose acetate, polymethyl methacrylate, polymethylsilsequioxane, talc, tetrafluoroethylene, silk powder, boron nitride, lauroyl lysine, synthetic oils, natural oils, esters, silicones, glycols, and the like. The composition of the present disclosure may suitably include one or more slip modifier in an amount of from about 0.01% (by weight of the composition) to about 20% (by weight of the composition).

The compositions of the disclosure may optionally further comprise surface modifiers. Examples of suitable surface modifiers include silicones, quaternium materials, powders, salts, peptides, polymers, clays, and glyceryl esters. The composition of the present disclosure may suitably include one or more surface modifier in an amount of from about 0.01% (by weight of the composition) to about 20% (by weight of the composition).

The compositions of the disclosure may optionally further comprise skin protectants. Examples of suitable skin protectants include ingredients referenced in SP monograph (21 CFR part 347). Suitable skin protectants and amounts include those set forth in SP monograph, Subpart B—Active Ingredients Sec 347.10: (a) Allantoin, 0.5 to 2%, (b) Aluminum hydroxide gel, 0.15 to 5%, (c) Calamine, 1 to 25%, (d) Cocoa butter, 50 to 100%, (e) Cod liver oil, 5 to 13.56%, in accordance with 347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1 to 30%, (h) Glycerin, 20 to 45%, (i) Hard fat, 50 to 100%, (j) Kaolin, 4 to 20%, (k) Lanolin, 12.5 to 50%, (l) Mineral oil, 50 to 100%; 30 to 35% in combination with colloidal oatmeal in accordance with §347.20(a)(4), (m) Petrolatum, 30 to 100%, (o) Sodium bicarbonate, (q) Topical starch, 10 to 98%, (r) White petrolatum, 30 to 100%, (s) Zinc acetate, 0.1 to 2%, (t) Zinc carbonate, 0.2 to 2%, (u) Zinc oxide, 1 to 25%.

The compositions of the disclosure may optionally further comprise particulates. Examples of suitable particulates include bismuth oxychloride, iron oxide, mica, surface treated mica, ZnO, $ZrO_2$, silica, silica silyate, colloidal silica, attapulgite, sepiolite, starches (i.e. corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, bismuth oxychloride, iron oxide, aluminum oxide, silicone resin, barium sulfate, clays, cellulosics, calcium carbonate, cellulose acetate, polymethyl methacrylate, polymethylsilsequioxane, talc, tetrafluoroethylene, silk powder, boron nitride, lauroyl lysine, aluminum starch octenylsuccinate, and calcium starch octenylsuccinate. The composition of the present disclosure may suitably include one or more particulate in an amount of from about 0.01% (by weight of the composition) to about 20% (by weight of the composition).

The compositions of the disclosure may optionally further comprise sunscreens. Examples of suitable sunscreens include aminobenzoic acid, avobenzone, cinoxate, dioxybenzone, homosalate, menthyl anthranilate, octocrylene, octinoxate, octisalate, oxybenzone, padimate O, phenylbenzimidazole sulfonic acid, sulisobenzone, titanium dioxide, trolamine salicylate, zinc oxide, and combinations thereof. Other suitable sunscreens and amounts include those approved by the FDA, as described in the Final Over-the-Counter Drug Products Monograph on Sunscreens (Federal Register, 1999:64:27666-27693), herein incorporated by reference, as well as European Union approved sunscreens and amounts.

The compositions of the disclosure may optionally further comprise quaternary ammonium materials. Examples of suitable quaternary ammonium materials include polyquaternium-7, polyquaternium-10, benzalkonium chloride, behentrimonium methosulfate, cetrimonium chloride, cocamidopropyl pg-dimonium chloride, guar hydroxypropyltrimonium chloride, isostearamidopropyl morpholine lactate, polyquaternium-33, polyquaternium-60, polyquaternium-79, quaternium-18 hectorite, quaternium-79 hydrolyzed silk, quaternium-79 hydrolyzed soy protein, rape seed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like. The composition of the present disclosure may suitably include one or more quaternary material in an amount of from about 0.01% (by weight of the composition) to about 20% (by weight of the composition).

The compositions of the disclosure may optionally further comprise surfactants. Examples of suitable surfactants include, for example, anionic surfactants, cationic surfactants, amphoteric surfactants, zwitterionic surfactants, nonionic surfactants, and combinations thereof. Specific examples of suitable surfactants are known in the art and include those suitable for incorporation into personal care compositions and wipes. The composition of the present disclosure may suitably include one or more surfactant in an amount of from about 0.01% (by weight of the composition) to about 60% (by weight of the composition) active surfactant. In embodiments where the composition is a liquid composition for use in a wet wipe, the composition will preferably comprise one or more surfactant in an amount of from about 0.01% (by weight of the composition) to about 20% (by weight of the composition) of active surfactant.

The compositions of the disclosure may optionally further comprise additional emulsifiers. As mentioned above, the modified sorbitan siloxanes may act as emulsifiers in the composition. Optionally, the composition may comprise an additional emulsifier other than the modified sorbitan siloxanes. Examples of suitable emulsifiers include nonionics such as polysorbate 20, polysorbate 80, anionics such as DEA phosphate, cationics such as behentrimonium methosulfate, and the like. The composition of the present disclosure may suitably include one or more additional emulsifier in an amount of from about 0.01% (by weight of the composition) to about 20% (by weight of the composition).

The compositions of the present disclosure may additionally include adjunct components conventionally found in pharmaceutical compositions in their art-established fashion and at their art-established levels. For example, the compositions may comprise additional compatible pharmaceutically active materials for combination therapy, such as antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, and combinations thereof. Other suitable additives that may be included in the compositions of the present disclosure include colorants, deodorants, fragrances, perfumes, emulsifiers, anti-foaming agents, lubricants, natural moisturizing agents, skin conditioning agents, skin protectants and other skin benefit agents (e.g., aloe vera and laponite), solvents, solubilizing agents, suspending agents, wetting agents, humectants, preservatives, propellants, dyes and/or pigments, and combinations thereof.

Having described the disclosure in detail, it will be apparent that modifications and variations are possible without departing from the scope of the disclosure defined in the appended claims.

EXAMPLES

The following non-limiting examples are provided to further illustrate the present disclosure.

Test Methods

Dynamic Coefficient of Friction: The dynamic coefficient of friction (COF) between the surfaces of a wet wipe and a simulated skin substrate is tested using the following method. The test uses a stationary sled with a moving plane to measure the relative difficulty with which the surface of one material (e.g., a wipe) will slide over an adjoining surface of either itself or another material, such as a simulated skin material. The kinetic or sliding coefficient of friction is related to the force measured in sustaining this movement. A Slip/peel tester (Imass, Inc., Accord, Mass., model SP-101B) is used to conduct the friction measurements.

To begin, the substrate to be tested (e.g., a wipe substrate) is cut into 67 mm (in the cross direction) by 152 mm (in the machine direction) pieces. A slit approximately 2 inches long is cut in the test substrate, centered on the substrate in the machine direction.

A piece of Vitro-Skin® synthetic skin substrate is placed onto the moveable plate (platen) of the Slip/peel tester. The test substrate is then attached to the sled by placing the sled on the test substrate and bringing the slit end of the substrate around the end of the sled that has an attachment screw, and taping both ends of the substrate to the sled.

The sled containing the test substrate is then placed in position on the platen. The experiment is carried out by pressing the start button on the Slip/peel instrument. When the Slip/peel instrument stops, the displayed value is recorded. A new piece of Vitro-Skin® substrate and test substrate is used for each test.

The dynamic COF value is calculated by dividing the displayed value (grams) by the sled weight (100 grams).

Airlaid Nonwoven Material Basesheets

A 44-49 gsm, 1.0 mm thick thermally-bonded airlaid (TBAL) fibrous material was cut into 10"×13" handsheets. The thermally-bonded airlaid material was prepared as described in U.S. Patent Application Publication No. 2004/0063888, which is incorporated herein by reference in its entirety. Using various binder compositions at 15% total solids, the TBAL handsheets were treated with a binder composition using a pressurized spray unit to achieve a final 24% total content of binder composition in the handsheets.

Wet Wipe Preparation and Aging Protocol

Each 10"×13" airlaid nonwoven material was die cut into two 7.5"×5.5" dry wipes, with the shorter direction being the machine-direction (MD) direction. A standard plastic pipette was used to apply 235% by weight average add-on of a wetting composition that is used on commercially available wet wipes under the trade designation KLEENEX® COTTONELLE FRESH® Folded Wipes (Kimberly-Clark Corporation of Neenah, Wis.) to each side of the wipe. A stack of 10 wetted wipes was then formed and placed into a plastic baggie. The stack of 10 wet wipes in the plastic bag was compressed using a 22 pound roller, by rolling the bag four times. The bag was then sealed and the compressed stack of TBAL wet wipes was then aged under 1000 g of weight for 3 days. The stack was then transferred to a 46° C. oven for an additional 24 h before testing.

180° T-Peel Measurements (Sheet-to-Sheet Adhesion)

A 180° t-peel measurement was used to determine the sheet-to-sheet adhesion between adjacent wet wipe surfaces. The method for the 180° t-peel measurement is based upon ASTM D1876-01 Standard Test Method for Peel Resistance of Adhesives (T-Peel Test) with the following modifications. A crosshead speed of 20 inches/minute with a gauge length of 1.5 inches was used for all measurements. Measurements were recorded between 0.5 inches and 6.0 inches, with the end test point at 6.5 inches. Wet wipes were aged prior to measurement according to the "Wet Wipe Preparation and Aging Protocol". The aged wipes were cut into samples 1" (in.) width and a depth of at least two layers thick. This protocol may also be used to determine the sheet-to-sheet adhesion of dry basesheets with the following modifications: in the case of dry basesheet, the aged basesheet measures 3" width, with a sample size of six used for measurement.

Wet-Wipe In-Use Tensile Strength Measurements

In-use wet tensile measurements were determined using a pneumatic grip gauge separation of 3" and a crosshead speed of 10"/min. The peak load values (g/in.) of sample replicates were recorded and averaged and reported as machine-direction in-use tensile strength.

Example 1

In this example, wet wipe compositions comprising modified sorbitan siloxanes were prepared. The composition components are listed in Table 1.

TABLE 1

| Trade name | INCI name | Composition (% weight) | | |
|---|---|---|---|---|
| | | 1 | 2 | 3 |
| Water | Water | 94.348% | 92.848% | 94.92% |
| Silicone ST-006-219A (Siltech) | Modified sorbitan siloxane | 1.5% | — | — |
| Silicone ST-006-226A (Siltech) | Modified sorbitan siloxane | — | 1.5% | — |
| Silicone ST-006-219B (Siltech) | Modified sorbitan siloxane | — | — | 0.5% |
| | Surfactant blend[1] | 4.152% | 4.152% | — |
| Sodium chloride | Sodium chloride | — | — | 2.0% |
| Xanthan gum | Xanthan gum | — | — | 0.2% |
| Plantapon LGC Sorb | Sodum lauryl glucose carboxylate (and) lauryl glucoside | — | — | 0.64% |
| Propylene glycol | Propylene glycol | — | — | 0.5% |
| Neolone 950 | Methylisothiazolinone | — | — | 0.09% |
| Sodium benzoate | Sodium benzoate | — | — | 0.45% |
| Betafin BP-20 | 2-trimethyl ammonioacetate | — | — | 0.2% |
| Meraquat 740 | Polyquaternium-7 | — | 1.5% | 0.5% |
| Malic acid, pH to 5.5 | Malic acid | adjust | adjust | adjust |

[1]Wetting composition used on HUGGIES ® wet wipes (commercially available from Kimberly-Clark Corporation).

The compositions were prepared by combining the water with surfactant/humectant/preservative blend (if present) followed by mixing until uniform. The modified sorbitan siloxane was then added, and the resulting mixture was mixed until uniform, followed by addition of any remaining composition components. The pH of compositions 1 and 2 was adjusted to about 5.5 using malic acid, as needed, while the pH of composition 3 was adjusted to about 4.40 using malic acid, as needed.

Example 2

In this example, the sheet-to-sheet adhesion, in-use tensile strength, and in-use stretch of wet wipes comprising a modified sorbitan siloxane of the present disclosure was determined using the methods described in the Test Methods section. Wet wipes were prepared as described in the Test Methods section, except the base sheet was that used for commercially available wet wipes sold under the name KLEENEX® COTTONELLE® FLUSHABLE MOIST WIPES or SCOTT® FLUSHABLE MOIST WIPES. Additionally, the wetting compositions used to prepare the wet wipes had added thereto either a modified sorbitan siloxane of the present disclosure (Treatments 2-6) or was a control containing no additive (Treatment 1). The type and amount of additive and results are set forth in Table 2.

TABLE 2

| Treatment | Additive (% by weight) | Sheet Adhesion[1] (gf/inch) | In-Use Tensile Strength[2] (MD) (gf/inch) | In-Use Stretch[2] (MD) (%) |
|---|---|---|---|---|
| 1 | None | 2.7 | 471.2 | 24.8 |
| 2 | Modified sorbitan siloxane (ST-006-219A) (1%) | 3.1 | 475.1 | 24.8 |
| 3 | Modified sorbitan siloxane (ST-006-226A) (1%) | 2.6 | 470.9 | 24.5 |
| 4 | Modified sorbitan siloxane (ST-006-219B) (0.5%) and polyquaternium-7 (0.5%) | 2.4 | 517.0 | 24.9 |
| 5 | Modified sorbitan siloxane (ST-006-226A-0.5% wt.) and polyquaternium-7 (1%) | 2.6 | 468.3 | 24.3 |
| 6 | Modified sorbitan siloxane (ST-006-226B) (2%) | 1.8 | 461.9 | 23.2 |

[1]Results for Treatments 2-5 are the average of 9 adhesion strength measurements for wipes in a stack of 10 wipes. Treatments 1 and 6 are the average of only 6 adhesion strength measurements, since three of the sheets in the stack for these treatments fell completely apart during testing.
[2]Results are the average of 8 measurements.

As can be seen from these results, the presence of a modified sorbitan siloxane in a wet wipe composition does not negatively impact sheet-to-sheet adhesion of wet wipes, and in some instances, lowers sheet adhesion.

The sheet-to-sheet adhesion, in-use tensile strength, and % in-use stretch tests were repeated for Treatment 6 using a raw, uncoated basesheet. The results are given in Table 3.

TABLE 3

| Treatment | Additive | Sheet Adhesion[1] (gf/inch) | In-Use Tensile Strength[2] (MD) (gf/inch) | In-Use Stretch[2] (MD) (%) |
|---|---|---|---|---|
| 6 | Modified sorbitan siloxane (ST-006-226B) | 4.7 | 475.2 | 26.3 |

[1]Result for Treatment 6 is the average of only 6 adhesion strength measurements, since three of the sheets in the stack fell completely apart during testing.
[2]Results are the average of 6 measurements.

The sheet-to-sheet adhesion strength for a control wet wipe having an uncoated basesheet and containing no modified sorbitan siloxane additive in the wet wipe composition is typically about 4.9 to 5.3 gf/inch (results not shown). As can be seen from the results obtained for Treatment 6, inclusion of a modified sorbitan siloxane in a wet wipe composition improves sheet adhesion as compared to untreated controls.

Example 3

In this example, a composition is prepared that comprises a modified sorbitan siloxane and is suitable for use in combination with a dry wipe. The composition components are listed in Table 4.

TABLE 4

| INCI name | Function | Weight % |
|---|---|---|
| Decyl glucoside (in water/aqua) | Emollient (carrier) | 55.194 |
| Glycerin (in water/aqua) | Humectant (carrier) | 19.819 |
| Cocamidopropyl betaine (in water/aqua) | Foaming surfactant (carrier) | 16.845 |
| Silicone ST-006-226A | Skin feel, emulsifier, surfactant, solubilizer | 4.954 |
| Citric acid | pH adjustment | 0.892 |
| DMDM hydantoin; iodopropynyl buctylcarbamate (in water/aqua) | Preservative (carrier) | 0.496 |
| Coco-glucoside, glyceryl oleate (in water/aqua) | Surfactant, emollient (carrier) | 1.00 |
| PEG-50 shea butter | Shea butter | 0.100 |
| Fragrance/parfum | fragrance | 0.700 |

Example 4

In this example, a composition is prepared that comprises a modified sorbitan siloxane and is suitable for use as a detangling and/or conditioning shampoo formulation. The composition components are listed in Table 5.

TABLE 5

| INCI Name | Function | Weight % |
|---|---|---|
| Water/aqua | Carrier | 69.12 |
| Decyl glucoside (in water/aqua) | Surfactant (carrier) | 10.00 |
| Silicone ST-006-226A | Modified sorbitan siloxane | 10.00 |
| Polyquaternium 7 | Conditioner | 10.00 |
| Citric acid | pH adjustment | 0.66 |
| Methylisothiazolinone/ methylchloroisothiazalinone (in water/aqua) | Preservative (carrier) | 0.07 |
| Fragrance/parfum | Fragrance | 0.15 |

Example 5

In this example, a composition is prepared that comprises a modified sorbitan siloxane and is suitable for use in combination with a dry wipe. The composition components are listed in Table 6.

TABLE 6

| INCI Name | Function | Weight % |
|---|---|---|
| Decyl glucoside (in water/aqua) | Surfactant (carrier) | 55.70 |
| Glycerin | Emollient | 19.80 |
| Silicone ST-006-226A | Modified sorbitan siloxane | 21.80 |
| Citric acid | pH adjustment | 0.90 |
| Coco-glucoside, glyceryl oleate (in water/aqua) | Surfactant, emollient (carrier) | 1.00 |
| PEG-500 shea butter | Shea butter | 0.10 |
| Fragrance/parfum | fragrance | 0.70 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A wet wipe for imparting a perceivable aesthetic feel to skin, the wipe comprising:
   a wipe substrate; and
   a liquid composition comprising a modified sorbitan siloxane having the following structure:

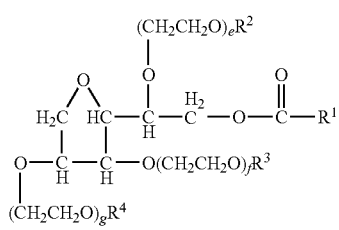

wherein $R^1$ is an alkyl having from 7 to 21 carbon atoms; $R^2$, $R^3$, and $R^4$ are independently selected from the group consisting of H and Structure 2:

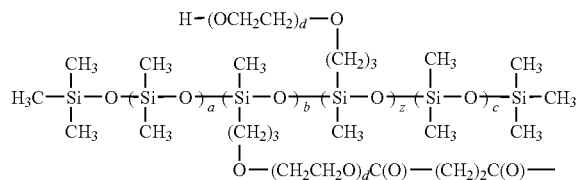

wherein at least one of $R^2$, $R^3$, or $R^4$ is Structure 2; a is an integer ranging from 0 to 200; b is an integer ranging from 1 to 10; z is an integer ranging from 1 to 10; c is an integer ranging from 0 to 10; d is an integer ranging from 5 to 20; n is an integer ranging from 7 to 17; e is an integer ranging from 0 to 30; f is an integer ranging from 0 to 30; g is an integer ranging from 0 to 30, wherein the sum of e, f, and g is an integer ranging from 9 to 50; and wherein the ratio of hydroxyl to carboxyl group ranges from 4:1 to 2:1.

2. The wet wipe of claim 1 wherein at least two of $R^2$, $R^3$, or $R^4$ is Structure 2.

3. The wet wipe of claim 1 wherein each of $R^2$, $R^3$, and $R^4$ is Structure 2.

4. The wet wipe of claim 1 wherein the liquid composition comprises from about 0.05% (by weight of the composition) to about 50.0% (by weight of the composition) of the modified sorbitan siloxane.

5. The wet wipe of claim 4 wherein the liquid composition comprises from about 0.1% (by weight of the composition) to about 25.0% (by weight of the composition) of the modified sorbitan siloxane.

6. The wet wipe of claim 1 wherein the liquid composition further comprises from about 75% (by weight of the composition) to about 99% (by weight of the composition) of water.

7. The wet wipe of claim 1 wherein the liquid composition further comprises from about 0.05% (by weight of the composition) to about 25% (by weight of the composition) of a humectant.

8. The wet wipe of claim 1 wherein the liquid composition further comprises a surfactant selected from the group consisting of anionic surfactants, cationic surfactants, amphoteric surfactants, zwitterionic surfactants, and combinations thereof in an amount of from about 0.01% (by weight of the composition) to about 20% (by weight of the composition) active surfactant.

9. The wet wipe of claim 1 wherein the liquid composition further comprises a skin benefit agent selected from the group consisting of a quaternary ammonium material, a particulate, a rheology modifier, a moisturizer, a film former, a slip modifier, a surface modifier, a skin protectant, a sunscreen, an emollient, and combinations thereof.

10. The wet wipe of claim 1 wherein the liquid composition further comprises an additional emulsifier.

11. The wet wipe of claim 1 wherein the liquid composition is present on the wipe in an add-on amount of from about 100% (by weight of the treated substrate) to about 400% (by weight of the treated substrate).

12. A composition for imparting a perceivable aesthetic feel to skin or hair, the composition comprising a carrier and a modified sorbitan siloxane having the following structure:

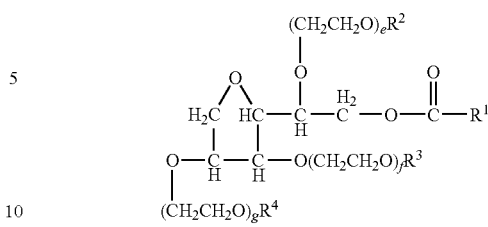

wherein $R^1$ is an alkyl having from 7 to 21 carbon atoms; $R^2$, $R^3$, and $R^4$ are independently selected from the group consisting of H and Structure 2:

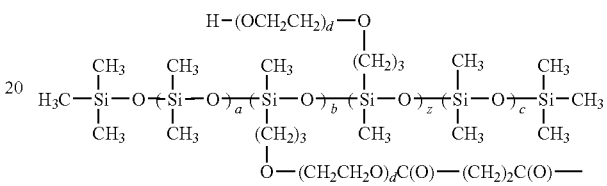

wherein at least one of $R^2$, $R^3$, or $R^4$ is Structure 2; a is an integer ranging from 0 to 200; b is an integer ranging from 1 to 10; z is an integer ranging from 1 to 10; c is an integer ranging from 0 to 10; d is an integer ranging from 5 to 20; n is an integer ranging from 7 to 17; e is an integer ranging from 0 to 30; f is an integer ranging from 0 to 30; g is an integer ranging from 0 to 30, wherein the sum of e, f, and g is an integer ranging from 9 to 50; and wherein the ratio of hydroxyl to carboxyl group ranges from 4:1 to 2:1.

13. The composition of claim 12 wherein at least two of $R^2$, $R^3$, or $R^4$ is Structure 2.

14. The composition of claim 12 wherein each of $R^2$, $R^3$, and $R^4$ is Structure 2.

15. The composition of claim 12 wherein the composition comprises from about 0.05% (by weight of the composition) to about 50% (by weight of the composition) of the modified sorbitan siloxane.

16. The composition of claim 15 wherein the composition comprises from about 0.1% (by weight of the composition) to about 25% (by weight of the composition) of the modified sorbitan siloxane.

17. The composition of claim 12 wherein the composition comprises from about 40% (by weight of the composition) to about 99% (by weight of the composition) of water.

18. The composition of claim 12 wherein the composition further comprises from about 0.05% (by weight of the composition) to about 25% (by weight of the composition) of a humectant.

19. The composition of claim 12 wherein the liquid composition further comprises a surfactant selected from the group consisting of anionic surfactants, cationic surfactants, amphoteric surfactants, zwitterionic surfactants, and combinations thereof in an amount of from about 0.01% (by weight of the composition) to about 60% (by weight of the composition) active surfactant.

20. The composition of claim 12 wherein the composition further comprises a skin benefit ingredient selected from the group consisting of a quaternary ammonium material, a particulate, a rheology modifier, a moisturizer, a film former, a slip modifier, a surface modifier, a skin protectant, a sunscreen, an emollient, and combinations thereof.

21. The composition of claim 12 wherein the composition further comprises an additional emulsifier.

22. A substantially dry wipe for imparting a perceivable aesthetic feel to skin, the substantially dry wipe comprising:
a wipe substrate; and
a composition comprising a modified sorbitan siloxane having the following structure:

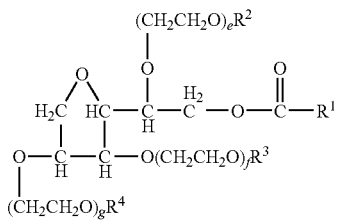

wherein $R^1$ is an alkyl having from 7 to 21 carbon atoms; $R^2$, $R^3$, and $R^4$ are independently selected from the group consisting of H and Structure 2:

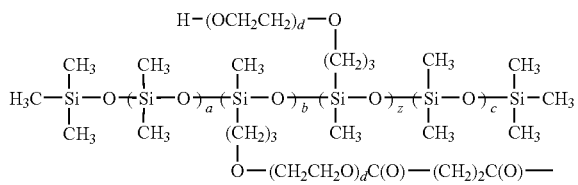

wherein at least one of $R^2$, $R^3$, or $R^4$ is Structure 2; a is an integer ranging from 0 to 200; b is an integer ranging from 1 to 10; z is an integer ranging from 1 to 10; c is an integer ranging from 0 to 10; d is an integer ranging from 5 to 20; n is an integer ranging from 7 to 17; e is an integer ranging from 0 to 30; f is an integer ranging from 0 to 30; g is an integer ranging from 0 to 30, wherein the sum of e, f, and g is an integer ranging from 9 to 50; and wherein the ratio of hydroxyl to carboxyl group ranges from 4:1 to 2:1.

23. The substantially dry wipe of claim 22 wherein the composition comprises from about 0.05% (by weight of the composition) to about 50% (by weight of the composition) of the modified sorbitan siloxane.

24. The substantially dry wipe of claim 22 wherein the composition further comprises a skin benefit agent selected from the group consisting of a quaternary ammonium material, a particulate, a rheology modifier, a moisturizer, a film former, a slip modifier, a surface modifier, a skin protectant, a sunscreen, an emollient, a humectant, and combinations thereof.

25. The substantially dry wipe of claim 22 wherein the composition further comprises a surfactant selected from the group consisting of anionic surfactants, cationic surfactants, amphoteric surfactants, zwitterionic surfactants, non-ionic surfactants, and combinations thereof in an amount of from about 0.01% (by weight of the composition) to about 60% (by weight of the composition) active surfactant.

\* \* \* \* \*